(12) United States Patent
Chen et al.

(10) Patent No.: US 7,659,248 B2
(45) Date of Patent: Feb. 9, 2010

(54) STABILIZED COMPOSITIONS COMPRISING TISSUE FACTOR PATHWAY INHIBITOR PROTEIN OR TISSUE FACTOR PATHWAY INHIBITOR VARIANT PROTEINS

(75) Inventors: Bao-lu Chen, San Ramon, CA (US); Chin-Yi Huang, Fremont, CA (US)

(73) Assignee: Novartis Vaccines and Diagnostics, Emeryville, CA (US)

( * ) Notice: Subject to any disclaimer, the term of this patent is extended or adjusted under 35 U.S.C. 154(b) by 792 days.

(21) Appl. No.: 11/302,208

(22) Filed: Dec. 14, 2005

(65) Prior Publication Data
US 2006/0079459 A1 Apr. 13, 2006

Related U.S. Application Data

(63) Continuation of application No. 10/753,068, filed on Jan. 8, 2004, now abandoned.

(60) Provisional application No. 60/512,090, filed on Oct. 20, 2003, provisional application No. 60/509,260, filed on Oct. 8, 2003, provisional application No. 60/494,577, filed on Aug. 13, 2003, provisional application No. 60/438,519, filed on Jan. 8, 2003.

(51) Int. Cl.
*A61K 38/00* (2006.01)

(52) U.S. Cl. ........................................ 514/12
(58) Field of Classification Search ............... 530/350
See application file for complete search history.

(56) References Cited

U.S. PATENT DOCUMENTS

| | | |
|---|---|---|
| 4,650,674 A | 3/1987 | Aggarwal et al. |
| 4,812,557 A | 3/1989 | Yasushi et al. |
| 4,883,661 A | 11/1989 | Daly et al. |
| 4,894,226 A | 1/1990 | Aldwin et al. |
| 4,931,543 A | 6/1990 | Halenbeck et al. |
| 5,034,225 A | 7/1991 | Bennett et al. |
| 5,078,997 A | 1/1992 | Hora et al. |
| 5,272,135 A | 12/1993 | Takrurl |
| 5,340,574 A | 8/1994 | Maneglier et al. |
| 5,358,708 A | 10/1994 | Patel |
| 5,744,132 A | 4/1998 | Warne et al. |
| 5,763,395 A | 6/1998 | Blackburn et al. |
| 5,795,779 A | 8/1998 | McCormick et al. |
| 5,888,968 A | 3/1999 | Chen et al. |
| 6,248,548 B1 * | 6/2001 | Veer et al. ..................... 435/13 |
| 6,525,102 B1 | 2/2003 | Chen et al. |
| 2002/0045571 A1 | 4/2002 | Liu et al. |
| 2002/0147184 A1 | 10/2002 | Kosoglou et al. |
| 2003/0092627 A1 | 5/2003 | Petersen et al. |

FOREIGN PATENT DOCUMENTS

| | | |
|---|---|---|
| EP | 0 229 016 A2 | 7/1987 |
| EP | 0 303 746 A1 | 2/1993 |
| IE | 921124 | 10/1992 |
| WO | WO 9604377 A1 * | 2/1996 |
| WO | WO 96/40784 A2 | 12/1996 |
| WO | WO 98/33920 A1 | 8/1998 |
| WO | WO 99/51272 A1 | 10/1999 |
| WO | WO 01/24814 A1 | 4/2001 |
| WO | WO 0136632 A2 * | 5/2001 |
| WO | WO 02094864 A2 * | 11/2002 |

OTHER PUBLICATIONS

GenCore search version 5.1.6, pp. 1-5.*
Allen et al., "Hybrid (BDBB) Interferon-Alpha.: Preformulation Studies," *Int J Pharm*, 1999, pp. 259-272, vol. 187.
Chang et al., "Development of a Stable Freeze-dried Formulation of Recombinant Human Interleukin-1 Receptor Antagonist," *Pharmaceutical Research*, 1996, pp. 243-249, vol. 13.
Chen et al., "Solubility of Recombinant Human Tissue Factor Pathway Inhibitor," *Journal of Pharmaceutical Sciences*, 1999, pp. 881-888, vol. 88.
Heller et al., "Manipulation of Lyophilization-Induced Phase Separation: Implications for Pharmaceutical Proteins," *Biotechnol Prog.*, 1997, pp. 590-596, vol. 13.
Taneja et al., "Increased Thermal Stability of Proteins in the Presence of Amino Acids," *Biochem J.*, 1994, pp. 147-153, vol. 303.
Wang et al., "Parenteral Formulations of Proteins and Peptides: Stability and Stabilizers," *Journal of Parenteral Science and Technology*, 1988, pp. S1-S26, vol. 42.

* cited by examiner

*Primary Examiner*—David J Steadman
(74) *Attorney, Agent, or Firm*—Leslie Fischer

(57) ABSTRACT

Stabilized aqueous compositions of tissue factor pathway inhibitor (TFPI) or TFPI variants comprise a solubilizing agent, an antioxidant, and a buffer. The combination of a solubilizing agent and an antioxidant can lead to a significant improvement in the storage life of TFPI or TFPI variant compositions. The solubilizing agent and antioxidant substantially counteract the effects of TFPI or TFPI variant degradation through aggregation and oxidation.

24 Claims, 7 Drawing Sheets

STABILIZED COMPOSITIONS COMPRISING TISSUE FACTOR PATHWAY INHIBITOR PROTEIN OR TISSUE FACTOR PATHWAY INHIBITOR VARIANT PROTEINS

CROSS-REFERENCE TO RELATED APPLICATIONS

This application is a continuation of U.S. application Ser. No. 10/753,068, filed Jan. 8, 2004, now abandoned. U.S. application Ser. No. 10/753,068 claims the benefit of priority of U.S. Provisional Application Ser. Nos. 60/438,519, filed Jan. 8, 2003; 60/494,577, filed Aug. 13, 2003; 60/509,260, filed Oct. 8, 2003; and 60/512,090, filed Oct. 20, 2003. All of the above nonprovisional and provisional applications are hereby incorporated by reference in their entireties.

FIELD OF THE INVENTION

The present invention relates to stabilized compositions comprising tissue factor pathway inhibitor protein (TFPI). More specifically, it relates to compositions comprising TFPI or a TFPI variant, a solubilizing agent, and an antioxidant.

BACKGROUND OF THE INVENTION

Tissue factor pathway inhibitor (TFPI) is 276 amino acids in length and functions as an inhibitor of tissue factor-mediated blood coagulation. Its amino acid sequence is shown in SEQ ID NO:1. The amino terminal end of TFPI is negatively charged, and the carboxy terminal end is positively charged. The TFPI protein contains three Kunitz-type enzyme inhibitor domains. TFPI contains 18 cysteine residues and forms 9 disulfide bridges when correctly folded. The primary sequence contains three N-linked consensus glycosylation sites (Asn-X-Ser/Thr). The asparagine residues of the glycosylation sites are located at positions 145, 195, and 256. TFPI is also known as lipoprotein associated coagulation inhibitor (LACI), tissue factor inhibitor (TFI), and extrinsic pathway inhibitor (EPI).

Use of TFPI has been proposed for the treatment of various indications, including sepsis (U.S. Pat. No. 6,063,764 and WO 93/24143), deep vein thrombosis (U.S. Pat. No. 5,563,123, U.S. Pat. No. 5,589,359, and WO 96/04378), ischemia (U.S. Pat. No. 5,885,781, U.S. Pat. No. 6,242,414, and WO 96/40224), restenosis (U.S. Pat. No. 5,824,644 and WO 96/01649), and cancer (U.S. Pat. No. 5,902,582 and WO 97/09063). A TFPI variant, which differs from TFPI by the addition of an alanine residue at the amino terminus ("ala-TFPI"), has been shown to be efficacious in animal models for the treatment of sepsis. Carr et al., Circ Shock November 1994; 44(3):126-37.

Following preparation, the compositions of TFPI or a TFPI variant can be packaged for storage in an aqueous form or in a frozen state. TFPI or TFPI variants, however, can form aggregates during storage in aqueous formulations. Aggregation is caused by interactions between the TFPI or TFPI variant molecules that result in the formation of oligomers. These oligomers may remain soluble or may form large, visible aggregates that precipitate from solution during storage. Aggregate formation by TFPI or TFPI variant during storage of an aqueous composition can adversely affect its biological activity, resulting in loss of therapeutic efficacy as an anti-coagulant effective for the treatment of a variety of conditions, including sepsis. Furthermore, aggregate formation may cause other problems, such as blockage of tubing, membranes, or pumps when the TFPI-containing or TFPI variant-containing composition is administered using an infusion system. To minimize these problems, there is a need in the art for improved stabilization of compositions of TFPI and TFPI variants.

SUMMARY OF THE INVENTION

The present invention is based on significant improvements in stability of aqueous compositions comprising TFPI or TFPI variants that are realized when such compositions comprise a solubilizing agent and an antioxidant. The antioxidant may be in the form of an oxygen displacement gas, an oxygen or free radical scavenger, or a chelating agent.

The invention provides at least the following embodiments.

One embodiment of the invention is an aqueous composition comprising about 0.05 to about 15 mg/ml of TFPI or TFPI variant; about 50 to about 600 mM of a solubilizing agent selected from the group consisting of (i) arginine or an analog thereof, (ii) lysine or an analog thereof, and (iii) mixtures of (i) and (ii); and an antioxidant selected from the group consisting of (i) an oxygen displacement gas, (ii) an oxygen or free radical scavenger, (iii) a chelating agent, and (iv) mixtures thereof; wherein the aqueous composition has (a) a percent aggregation stability of about 45% or greater; (b) a percent oxidation stability of about 45% or greater; and (c) a pH from about 4 to about 8.

Another embodiment of the invention is a method for making an aqueous TFPI or TFPI variant composition comprising the step of adding to an aqueous composition comprising about 0.05 to about 15 mg/ml TFPI or TFPI variant; about 50 to about 600 mM of a solubilizing agent selected from the group consisting of (i) arginine or a derivative thereof, (ii) lysine or a derivative thereof, and (iii) mixtures of (i) and (ii); and b) an antioxidant selected from the group consisting of (i) an oxygen displacement gas, (ii) an oxygen or free radical scavenger, (iii) a chelating agent, and (iv) mixtures of (i), (ii), and (iii, wherein the aqueous composition has (a) a percent aggregation stability of about 45% or greater; (b) a percent oxidation stability of about 45% or greater; and (c) a pH from about 4 to about 8.

Yet another embodiment of the invention is a pharmaceutical composition, comprising a) the aqueous composition and a pharmaceutically acceptable excipient. The aqueous composition comprises comprising about 0.05 to about 15 mg/ml of TFPI or TFPI variant; about 50 to about 600 mM of a solubilizing agent selected from the group consisting of (i) arginine or an analog thereof, (ii) lysine or an analog thereof, and (iii) mixtures of (i) and (ii); and an antioxidant selected from the group consisting of (i) an oxygen displacement gas, (ii) an oxygen or free radical scavenger, (iii) a chelating agent, and (iv) mixtures thereof; wherein the aqueous composition has (a) a percent aggregation stability of about 45% or greater; (b) a percent oxidation stability of about 45% or greater; and (c) a pH from about 4 to about 8.

DETAILED DESCRIPTION OF THE INVENTION

Figure 1:
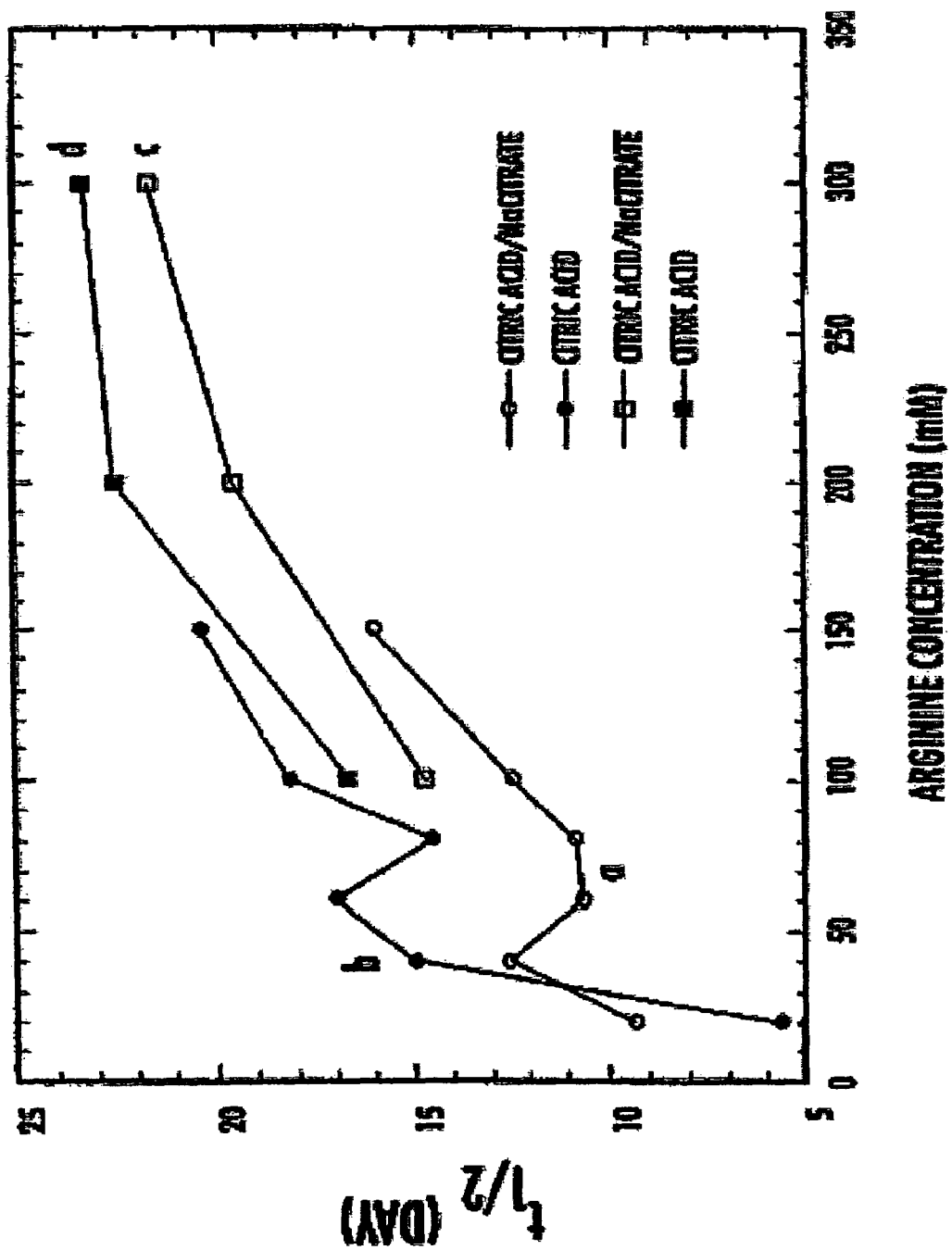
FIG. 1 shows the half-life during storage ($t_{1/2}$, in days) of four standard ala-TFPI compositions analyzed by ion-exchange high pressure liquid chromatography (IEX-HPLC) as a function of arginine concentration at 50° C. All formulations contained 0.15 mg/ml ala-TFPI buffered to pH 5.5 with either L-arginine base and citric acid or L-arginine HCl and 10 mM critic acid/sodium citrate. The specific ala-TFPI formulations contained: (a) 20-150 mM L-arginine HCl, 10 mM citric acid/sodium citrate as buffer; (b) 20-150 mM L-arginine base, titrated with citric acid; (c) 100-300 mM L-arginine HCl, 10 mM citric acid/sodium citrate as buffer; (d) 100-300 mM L-arginine base titrated with citric acid.

Aqueous compositions of the present invention are based on the discovery that the addition to an aqueous TFPI or TFPI variant composition of i) an amino acid solubilizing agent (e.g., arginine, lysine, or analogs thereof) and ii) an antioxidant, wherein the aqueous composition has a pH from about 4 to about 8, results in a TFPI-containing or TFPI variant-containing composition that has substantially increased stability during storage relative to TFPI-containing or TFPI variant-containing compositions prepared without the combination of these two additional components. This overall increased stability of the composition is achieved through the influence of the solubilizing agent combined with that of the antioxidant to provide a composition that resists not only aggregation during storage but also detrimental oxidation, especially at the TFPI methionine residues. Aqueous compositions of the invention also resist other detrimental effects (e.g., unfolding, refolding, and denaturation) that result in a loss of biological activity or other undesirable characteristics.

Because the solubilizing agent and antioxidant primarily affect independent mechanisms of TFPI or TFPI variant degradation (aggregation and methionine oxidation, respectively), the combination of the solubilizing agent and antioxidant provides a more stable TFPI or TFPI variant composition than possible without this combination, or even without one of these two components. For example, oxidation of TFPI or TFPI variant methionines may be undesirable even when the TFPI or TFPI variant is biologically active.

Stability of Aqueous Compositions

Aqueous TFPI-containing or TFPI variant-containing compositions of the invention typically have increased stability during storage with respect to one or more TFPI, degradation effects (e.g., aggregation and methionine oxidation) relative to compositions prepared in the absence of the combination of a solubilizing agent and an antioxidant as described herein. That is, because TFPI and TFPI variant containing compositions of the invention have an increased percent aggregation stability and increased percent oxidation stability, the half-life of unaggregated, unoxidized TFPI or TFPI variant is increased. The percent aggregation stability and the percent oxidation stability of a TFPI or TFPI variant sample can vary independently. Preferably, the TFPI or TFPI variant in aqueous compositions of the invention is biologically active, as determined, for example, by a prothrombin time assay, as described below.

Aqueous compositions of the invention have at least 45% aggregation stability. "Percent aggregation stability" refers to the proportion of a TFPI or TFPI variant sample that is soluble as measured in a 40° C. accelerated stability assay. In a 40° C. accelerated stability assay, a TFPI or TFPI variant sample is incubated for eight weeks at 40° C. Following incubation, the TFPI or TFPI variant sample is filtered through a 0.2 µm filter and subjected to an ion exchange high performance liquid chromatography (IEX-HPLC) assay to determine the amount of soluble TFPI or TFPI variant remaining in solution. An IEX-HPLC assay is described below 45%. Thus, for example, a TFPI or TFPI variant composition that has 60% aggregation stability is a composition in which 60% of the TFPI or TFPI variant is soluble as measured in the 40° C. accelerated stability assay. A TFPI or TFPI variant composition that has 80% aggregation stability is a composition in which 80% of the TFPI or TFPI variant is soluble as measured in the 40° C. accelerated stability assay. The percent aggregation stability of TFPI or TFPI variant compositions of the invention preferably is about 45, 50, 60, 70, or 75% or greater, more preferably about 80, 82, 84, 85, 90, 92, 94, 95, 96, 97, 98, or 99% or greater as measured in the 40° C. accelerated stability assay and can range, for example, from about 45% or greater to about 99% or greater, about 45% or greater to about 70% or greater, about 60% or greater to about 80% or greater, about 70% or greater to about 90% or greater, about 80% or greater to about 90% or greater, or about 45% or greater to about 70% or greater as measured in the 40° C. accelerated stability assay.

Aqueous compositions of the invention also have about 45% or greater oxidation stability. "Percent oxidation stability" refers to the proportion of TFPI or TFPI variant sample that does not contain an oxidized methionine as measured in a 30° C. accelerated stability assay. In the 30° C. accelerated assay, a TFPI or TFPI variant sample is incubated for eight weeks at 30° C. Following incubation, the TFPI or TFPI variant sample is subjected to a reverse phase-high performance liquid chromatography (RP-HPLC) assay to determine the amount of methionine-oxidized TFPI or TFPI variant present in the solution. An RP-HPLC assay is described below. Thus, for example, a TFPI or TFPI variant composition that has 60% oxidation stability is a composition in which 60% of the TFPI or TFPI variant does not contain an oxidized methionine as measured in the 30° C. accelerated stability assay. A TFPI or TFPI variant composition that has 80% oxidation stability is a composition in which 80% of the TFPI or TFPI variant does not contain an oxidized methionine as measured in the 30° C. accelerated stability assay. The percent oxidation stability of TFPI or TFPI variant compositions of the invention preferably is about 45, 50, 60, 70, or 75% or greater, more preferably about 80, 82, 84, 85, 89, 90, 91, 92, 94, 95, 96, 97, 98, or 99% or greater as measured in the 30° C. accelerated stability assay and can range, for example, from about 45% or greater to about 99% or greater, about 45% or greater to about 70% or greater, about 60% or greater to about 80% or greater, about 70% or greater to about 90% or greater, or about 80% or greater to about 90% or greater as measured in the 30° C. accelerated stability assay.

The half-life during storage of TFPI or TFPI variant in compositions of the present invention is typically in the range of about 1 to about 36 months (e.g., up to about 1, 2, 3, 4, 5, 10, 15, 20, 25, 30, 35, or 36 months), depending on the storage temperature. Aqueous compositions comprising TFPI or a TFPI variant, a solubilizing agent, and an antioxidant and having a pH of about 4 to about 8 in accordance with the present invention will typically have a half-life during storage with respect to aggregation and/or oxidation stability, of greater than about 8 weeks at a temperature of about 15° C. For example, the half-life during storage of TFPI or the TFPI variant is from about 1 month to about 24 months (e.g., about 1, 2, 4, 6, 8, 10, 12, 14, 16, 18, 20, 22, or 24 months) at a temperature of about 15° C. or about 30° C.

Storage Temperature

Increased storage stability is achieved whether the aqueous compositions of the invention are stored as liquids for later use or are frozen and thawed prior to use. Storage temperatures can range from about −70° C. to about 25° C. (e.g., about −70, −60, −50, −40, −30, −20, −10, 0, 1, 2, 3, 4, 5, 6, 7, 8, 9, 10, 12, 15, 18, 20, 21, 22, 23, 24, or 25° C.). Preferably, aqueous compositions of the invention are stored in their liquid form to take full advantage of the convenience of having increased storage stability in this form, ease of administration without reconstitution, and ability to supply the formulation in prefilled, ready-to-use syringes or as multidose preparations if the formulation is compatible with bacteriostatic agents. A preferred storage temperature for liquid formulations is about 2° C. to about 8° C. (e.g., about 2, 3, 4, 5, 6, 7, or 8° C.).

TFPI and TFPI Variants

TFPI is a polypeptide having the amino acid sequence shown in SEQ ID NO:1. Preferably, TFPI is a recombinant human protein generated in a microbial host. TFPI is further characterized and described with respect to its biological activity in WO 01/24814.

TFPI variants include analogs and derivatives of TFPI, as well as fragments of TFPI TFPI analogs, and TFPI derivatives. TFPI variants can be obtained from human or other mammalian sources, synthesized, or obtained by recombinant techniques. Analogs are TFPI molecules with one or more amino acid substitutions, insertions, deletions, and/or additions. Conservative substitutions, in which an amino acid is exchanged for another having similar properties, are preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr. They typically fall in the range of about 1 to 5 amino acids (e.g., 1, 2, 3, 4, or 5 amino acids). Additional amino acids can be added at any position in the molecule, particularly at the amino- or carboxy terminus. For example, one TFPI analog, N-L-alanyl-TFPI ("ala-TFPI"), has an additional alanine residue at the amino terminal end. Amino acid additions may be 1, 2, 5, 10, 25, 100, or more additional amino acids. Fusion proteins are encompassed within the definition.

Fragments are portions of TFPI, TFPI analogs, or TFPI derivatives. Examples of fragments include Kunitz domains 1, 2, or 3, Kunitz domains 1 and 2 or 2 and 3, or deletions of the N-terminus, C-terminus or both. Substantial guidance for making variants is found in U.S. Pat. No. 5,106,833. Fragments of TFPI comprise at least 20 consecutive amino acids of SEQ ID NO:1. For example, a fragment can be 20, 25, 30, 50, 100, 150, 200, 250, or 275 consecutive amino acids in length. TFPI fragments not possessing biological activity are described in U.S. Pat. No. 5,106,833. Use of such fragments in the present invention is also contemplated.

Derivatives are defined as TFPI, TFPI analogs, or TFPI fragments having additional moieties. Examples of such additions include glycosylation, phosphorylation, acetylation, or amidation.

Percent homology between a TFPI variant and SEQ ID NO:1 is determined using the Blast2 alignment program (Blosum62, Expect 10, standard genetic codes, open gap 11, extension gap 1, gap x_dropoff 50, and low complexity filter off). TFPI variants will generally have about 70% or greater, preferably about 80% or greater, more preferably about 90% to 95% (e.g., 90, 91, 92, 93, 94, or 95%) or greater, and most preferably about 98% or 99% amino acid sequence identity to SEQ ID NO:1.

Amino acid sequence variants of TFPI can be prepared by making alterations in a DNA sequence encoding TFPI. Methods for making nucleotide sequence alterations are well known in the art. See, for example, Walker and Gaastra, eds. (1983) *Techniques in Molecular Biology* (MacMillan Publishing Company, New York), Kunkel (1985) *Proc. Natl. Acad. Sci. USA* 82:488492, Kunkel et al. (1987) *Methods Enzymol.* 154:367-382, Sambrook et al. (1989) *Molecular Cloning: A Laboratory Manual* (Cold Spring Harbor, N.Y.), U.S. Pat. No. 4,873,192, and references cited therein.

TFPI variants preferably possess a substantial amount of biological activity, for example 10%, 30%, 50%, 60%, 80%, 90% or more of the biological activity of TFPI as measured, for example, in a prothrombin (PT) assay, described below. Obviously, any alterations made in the DNA encoding a TFPI variant must not place the sequence out of reading frame and preferably will not create complementary regions that could produce secondary mRNA structure. Guidance in determining which amino acid residues can be substituted, inserted, or deleted without abolishing biological or immunological activity of TFPI or TFPI variant can be found using computer programs well known in the art, such as DNASTAR software, or in Dayhoff et al. (1978) in *Atlas of Protein Sequence and Structure* (Natl. Biomed. Res. Found., Washington, D.C.). Stabilization of TFPI variants that are not biologically active also is contemplated.

TFPI or TFPI variants may be produced recombinantly as shown in U.S. Pat. No. 4,966,852. For example, a cDNA for the desired protein can be incorporated into a plasmid for expression in prokaryotes or eukaryotes. There are many references known to those skilled in the art that provide details on expression of proteins using microorganisms. See U.S. Pat. No. 4,847,201 and Maniatas et al., 1982, MOLECULAR CLONING: A LABORATORY MANUAL (Cold Spring Harbor, N.Y.).

A variety of techniques are available for transforming microorganisms and using the transformed microorganism to express TFPI or TFPI variants. The following are merely examples of possible approaches. TFPI or TFPI variant DNA sequences can be connected to appropriate control sequences. TFPI or TFPI variant DNA sequences can be incorporated into a plasmid, such as pUC13 or pBR322, which are commercially available from companies such as Boehringer-Mannheim. Once the TFPI or TFPI variant DNA is inserted into a vector, it can be cloned into a suitable host. The DNA can be amplified by techniques such as those shown in U.S. Pat. No. 4,683,202 and U.S. Pat. No. 4,683,195. cDNA may be obtained by inducing cells, such as HepG2 or SKHep hepatoma cells, to make mRNA, then identifying and isolating the mRNA and reverse transcribing it to obtain cDNA. After the expression vector is transformed into a host such as *E. coli*, the bacteria may be cultured and the protein expressed. Bacteria are preferred prokaryotic microorganisms, and *E.* coli is especially preferred. A preferred microorganism useful in the present invention is *E. coli* K-12, strain MM294 deposited under the provisions of the Budapest Treaty on Feb. 14, 1984 with the American Type Culture Collection, now located at 10801 University Blvd., Manassas, Va. (Accession Number 39607).

TFPI or TFPI variants may be produced in bacteria or yeast and subsequently purified. Generally, procedures can be employed as shown in U.S. Pat. No. 5,212,091, U.S. Pat. No. 6,063,764, and U.S. Pat. No. 6,103,500 or WO 96/40784. TFPI or TFPI variants can be purified, solubilized, and refolded according to WO 96/40784 and Gustafson et al., *Prot. Express. Pur.* 5:233 (1994). For example, when prepared according Example 9 of WO 96/40784, preparations of ala-TFPI are obtained that contain from about 85% to 90% of the total protein by weight as biologically active ala-TFPI.

TFPI or TFPI variant is typically added to aqueous compositions of the present invention in an amount from about 0.05 mg/ml to about 15 mg/ml (e.g., 0.05, 0.15, 0.5, 1, 2.5, 5, 7.5, 10, 12.5, or 15 mg/ml).

Amino Acid Solubilizing Agent

An amino acid solubilizing agent incorporated into TFPI-containing or TFPI variant-containing compositions of the present invention primarily protects TFPI or the TFPI variant from aggregation, thereby increasing its stability during storage. Decreased aggregate formation with the addition of the amino acid solubilizing agent occurs in a concentration dependent manner. That is, an increasing concentration of an amino acid solubilizing agent leads to increased stability of a TFPI or TFPI variant composition due to the corresponding reduction in aggregate formation during storage.

Preferred amino acid solubilizing agents are arginine, lysine, or arginine- or lysine-analogs. Arginine or lysine may be present either in a free base form or in a salt form, for example the hydrochloric acid salt form. Arginine or lysine analogs may also be in free base or salt forms. Arginine analogs include, for example, aminoguanidine arginine ethyl ester, arginine hydroxamate, and arginine p-nitroanilide. Lysine analogs include, for example, lysinamide, lysine ethyl ester, lysine hydroxamate, and lysine p-nitroanilide. Preferably, the solubilizing agent is arginine present in either its free base form or as its hydrochloride salt form. Also preferred for use as solubilizing agents, are the naturally occurring L-stereoisomers of arginine or lysine, although stabilized compositions of the present invention may incorporate the D-stereoisomers or mixtures of L- and D-stereoisomers.

Arginine or lysine solubilizing agents or their analogs are incorporated into the aqueous composition in an amount that brings about the desired effect of stabilizing the TFPI or TFPI variant compositions during storage, such that, relative to a similar composition but without added solubilizing agent, the formulation exhibits improved resistance to degradation. Preferably, the total amount of solubilizing agent in the composition is from about 50 to about 600 mM (e.g., 50, 100, 150, 200, 250, 300, 350, 400, 450, 500, 550, or 600 mM), more preferably from about 100 mM to about 400 mM, and most preferably about 300 mM.

Determination of the amount of a particular amino acid base to be added to a TFPI-containing or TFPI variant-containing aqueous composition to decrease aggregate formation, increase polypeptide stability, and increase storage stability of the composition, can readily be determined using methods generally known to one of skill in the art and described, for example, in Example 6, below. For example, the effect of either an arginine or lysine solubilizing agent on TFPI or TFPI variant stability during storage in an aqueous composition can be readily determined by measuring change in one or more of a number of possible properties of the TFPI or TFPI variant composition over time, such as, for example, the concentration of soluble polypeptide. An amount of soluble polypeptide in solution can be quantified by ion exclusion (IEC)-HPLC. In cases where the major route to TFPI or TFPI variant degradation is aggregation, an effective amount of solubilizing agent to incorporate within a TFPI-containing or TFPI variant-containing composition to obtain improved stability is an amount that resulted in decreased aggregate formation over time, and hence greater retention of soluble polypeptide in solution in its nonaggregated (i.e., monomeric) molecular form.

Antioxidants

Aqueous TFPI or TFPI variant compositions of the present invention also comprise an antioxidant. An "antioxidant" is a component that reduces oxidation of the TFPI or TFPI variant, especially the methionine amino acid residues within the molecule. Oxidation of methionine residues present in the TFPI or TFPI variant molecule is one of the major degradation pathways during storage of TFPI or TFPI variant compositions. Oxidation is related to the presence of contaminants in the composition that either react with methionine residues directly or that catalyze oxidation reactions. Therefore, the use of certain additive antioxidants to combat the effects of such contaminants leads to a far greater stability of TFPI or TFPI variant compositions, even of compositions that already incorporate a solubilizing agent according to the invention. Preferably, the antioxidant is pharmaceutically acceptable and is present in a concentration from about 0.01 to about 50 mM (e.g., about 0.01, 0.1, 1, 2, 5, 10, 15, 20, 25, 30, 35, 40, 45, or 50 mM), more preferably from about 1 to about 10 mM (e.g., about 1, 2, 3, 4, 5, 6, 7, 8, 9, or 10 mM). The term "pharmaceutically acceptable" means there are no significant adverse biological effects when the formulation is administered to a patient. The term "patient" encompasses both human and veterinary patients.

Three general types of antioxidants are effective in TFPI or TFPI variant compositions of the present invention are: oxygen displacement gases, oxygen or free radical scavengers, and chelating agents.

Oxygen Displacement Gases

Dissolved oxygen present in an aqueous TFPI or TFPI variant composition can ultimately lead to methionine oxidation and consequently either the loss of TFPI effectiveness for its intended therapeutic function or the incorporation of oxidized species (e.g., methionine sulfoxide) within the TFPI or TFPI variant polypeptide that may have unknown or undesirable physiological effects. Oxygen displacement gases are gases that are effective for purging or displacing the dissolved oxygen. Preferably, an oxygen displacement gas will reduce the soluble oxygen concentration significantly relative to the dissolved oxygen concentration when the composition is equilibrated in air at ambient conditions. Preferably the oxygen displacement gas reduces the dissolved oxygen concentration to less than about 10% relative to a dissolved oxygen concentration of an aqueous composition of TFPI or TFPI variant that does not comprise the oxygen displacement gas. This condition dramatically enhances stability.

Preferred oxygen displacement gases are substantially inert with respect to the TFPI or TFPI variant composition, i.e., no significant amount of chemical reactivity occurs upon exposure of the TFPI composition to the oxygen displacement gas, such that the biological activity of the TFPI is maintained. Suitable oxygen displacement gases include nitrogen, nitrogen-enriched air, nitrogen-enriched oxygen, noble gases (e.g., helium or argon), methane, ethane, propane, carbon dioxide, and mixtures of these gases. "Nitrogen enriched air" and "nitrogen enriched oxygen" are mixtures of nitrogen and air or oxygen, respectively, having a nitrogen concentration greater than that found in the atmosphere (i.e., greater than about 79 vol-%). Nitrogen is a preferred oxygen displacement gas.

The oxygen displacement gas may be present in any concentration in the composition up to and including its solubility limit. Solubility of an oxygen displacement gas in a TFPI or TFPI variant composition can be increased by maintaining the composition in a pressurized atmosphere, such as in a closed container containing the displacement gas above the liquid level of the composition. Alternatively, sub-atmospheric pressure can be maintained in the headspace to reduce solubility of an oxygen displacement gas.

Oxygen displacement gases may be introduced into a TFPI or TFPI variant composition in any conventional manner, such as by purging the headspace above the liquid level in a vial or other container holding the TFPI or TFPI variant composition with the displacement gas, sparging or bubbling the displacement gas through the TFPI or TFPI variant composition, using pressurization/depressurization cycles with the displacement gas, evacuating followed by repressurization with the displacement gas, and the like.

After oxygen displacement is effected as described above, re-solubilization of oxygen in the TFPI or TFPI variant composition is prevented by its isolation from air by the oxygen displacement gas.

Scavengers of Oxygen or Free Radicals

Another type of antioxidant useful in the present invention is an oxygen scavenger or a free radical scavenger. In general, such scavengers are more reactive with oxygen and/or free radicals than a TFPI or TFPI variant. They serve as "sacrificial" molecules that react with available oxygen, thereby preventing detrimental oxygen-TFPI or oxygen-TFPI variant interactions, most notably the oxidation of methionine residues. In a preferred embodiment, the oxygen or free radical scavenger having a concentration from about 0.1 to about 10 mM.

Suitable scavengers of oxygen or free radicals are stable in the TFPI or TFPI variant compositions of the present invention. Preferred pharmaceutically acceptable oxygen or free radical scavengers include methionine, ascorbic acid or sodium ascorbate, L-, DL- or D-alpha tocopherol and L-, DL- or D-alpha tocopherol acetate, betacarotene, selenium, pyritinol, propyl gallate, butylated hydroxyanisole (BHA), and butylated hydroxytoluene (BHT). The appropriate phase for the oxygen or free radical scavenger will naturally depend on its compatibility with a TFPI or TFPI variant composition. Generally hydrophilic antioxidants such as ascorbic acid or the acetate salt of alpha-tocopherol (i.e., alpha tocopherol acetate) may appropriately be incorporated into compositions of the present invention.

Any stereoisomer of methionine (L-, D-, or DL-isomer) or combination of isomers can be used. An especially preferred antioxidant is methionine, particularly L-methionine. Generally, superior results are obtained when the added methionine represents at least an amount equivalent on a molar basis to that present in TFPI or TFPI variant. In its native form, TFPI contains 5 methionine residues per protein molecule. Methionine that is part of the TFPI or TFPI variant protein is termed "TFPI or TFPI variant methionine" to distinguish it from that methionine added to the composition as an antioxidant and which is not part of the TFPI or TFPI variant protein. Of course, methionine in a polypeptide that is not TFPI or TFPI variant methionine can also serve as an oxygen scavenger for purposes of the present invention. For example, a polypeptide comprising poly(methionine) could reduce the rate of TFPI or TFPI variant methionine oxidation in a manner similar to free methionine added to the composition. Therefore, it is important to distinguish "TFPI or TFPI variant methionine" as defined above from "non-TFPI or non-TFPI variant" methionine, which includes any methionine residues added to the composition either in their free form or bound in a polypeptide that is not TFPI or TFPI variant.

Preferably, the methionine is present in an amount such that the molar ratio of non-TFPI or non-TFPI variant methionine to TFPI or TFPI variant methionine is from about 1:1 to about 10,000:1, more preferably from about 1:1 to about 5,000:1, even more preferably from about 100:1 to about 1,000:1, still even more preferably from about 300:1 to about 1,000:1, and yet even more preferably about 500:1 to about 1,000:1. In terms of its absolute concentration, methionine is preferably present in the composition in a concentration from about 1 to about 10 mM (e.g., about 1, 2, 3, 4, 5, 6, 7, 8, 9, or 10 mM). However, the concentration of methionine used may vary depending on the concentration of TFPI or TFPI variant in compositions of the invention. An important effect of methionine or other oxygen scavengers is to prevent the formation of TFPI or TFPI variant methionine sulfoxide residues that may cause undesired or unknown effects under physiological conditions, even in cases where the TFPI or TFPI variant may be biologically active. Thus, the amount of antioxidant to be added should be an amount sufficient to inhibit oxidation of the methionine residues such that the amount of methionine sulfoxide, generated upon oxidation of added methionine, is acceptable to regulatory agencies. Typically, this means that the composition contains no more than about 10% to about 30% of methionine residues as methionine sulfoxide.

Chelating Agents

Another type of antioxidant useful in the present invention is a chelating agent, also known as a sequestrant, which effectively binds transition metals ions (e.g., $Fe^{+3}$). Transition metal ions may be present in the composition and can catalyze detrimental oxidation reactions that lead to protein degradation and aggregation. Chelating agents are selected to have little or no chemical reactivity with the other components of the composition and to be generally compatible with the maintenance of desired physiological properties of the composition (e.g., pH and osmolarity). Therefore, it is preferred that chelating agents are used in compositions where transition metal cations are not deliberately added to the composition for purposes such as the maintenance or pH or osmolarity.

Chelating agents are preferably pharmaceutically acceptable. Preferred pharmaceutically acceptable chelating agents include the various amino carboxylate compounds that have the capacity to form metal-ligand complexes with one or more transition metal ions in solution. Such amino carboxylates include ethylenediaminetetraacetic acid (EDTA) and diethyltriaminepentaacetic (DTPA), 1,2-bis(2-aminophenoxy)ethane-N,N,N',N'-tetraacetic acid (BAPTA), ethylene glycol-bis(2-aminoethyl)-N,N,N',N'-tetraacetic acid (EGTA), and other amino carboxylate compounds having one or multiple carboxylate groups. Any derivative salt form of these amino carboxylate chelating agents, for example the disodium salt form, may be also used, provided that some capacity remains for the chelating agent to complex with free transition metal ions present in the TFPI or TFPI variant composition. Forms of these chelating agents other than salt forms are also effective and include the various ester, anhydride, and halogenated forms of these compounds.

Buffer

The pH of TFPI or TFPI variant compositions affects the solubility of the protein and hence its stability. See Chen et al. (1999) *J. Pharm. Sciences* 88(9):881-888. A preferred range of pH for the composition of the present invention is from about 4 to about 8 (e.g., 4, 4.5, 5, 5.5, 6, 6.5, 7, 7.5, or 8), more preferably from about 5 to about 6.5. Because pH is a significant factor in TFPI solubility, use of a buffer to maintain the proper pH can additionally improve the stability of the formulations. Thus, aqueous compositions of the present invention can further comprise a buffer to maintain solution pH. Preferably, the buffer is an acid substantially free of its salt form, an acid in its salt form, or a mixture of an acid and its salt-form.

Preferably, the pH of the composition is maintained using an arginine or lysine amino acid solubilizing agent in its base form in combination with an acid substantially free of its salt form. Such a combination provides for a lower osmolarity of the solution than if an acid and its salt form are used as a buffer in combination with an amino acid base. The advantage of such a combination is that one can incorporate a higher concentration of the arginine or lysine amino acid solubilizing agent and/or antioxidant (e.g., methionine) into an aqueous composition without exceeding isotonicity of the solution. An "acid substantially free of its salt form" means that an acid serving as the buffering agent within the aqueous composition typically contains less than about 2% of its salt forms.

Typically, when a buffer comprising an acid is used in an aqueous composition, it is prepared using a salt form of the acid or a combination of the acid and a salt form of the conjugate base of the acid. Thus, for example, the buffer may be prepared using the acid with the sodium, potassium, ammonium, calcium, and/or magnesium salt of its conjugate base. Where the buffer is chosen to comprise the base form of the arginine or lysine solubilizing agent in combination with an acid substantially free of its salt form, preferred buffers are selected from citric acid, succinic acid, phosphoric acid, glutamic acid, maleic acid, malic acid, acetic acid, tartaric acid, and aspartic acid. Citric acid and succinic acid are especially preferred for use as a buffer in combination with arginine in its free base form. Otherwise, as mentioned previously, arginine may be used in its salt form, such as the HCl salt form of arginine. In this case, the buffer will generally comprise a combination of an acid as described above and a salt form of its conjugate base. Other buffers that may be used include histidine and imidazole. Overall, preferred concentrations of the buffer are from about 0 to about 50 mM (e.g., 0, 1, 2, 5, 10, 15, 20, 25, 30, 35, 40, 45, or 50 mM); more preferred concentrations are from about 5 to about 30 mM.

If the buffer used is an amino acid base and an acid substantially free of its salt form, TFPI-containing or TFPI variant-containing compositions may be prepared that are substantially isotonic without having to include additional isotonizing agents, such as sodium chloride. A composition that is substantially isotonic causes only a minimal flow of water or no flow of water across the membranes of surrounding cells after in vivo administration. In general, isotonicity of aqueous compositions is desirable as it reduces pain upon administration and minimizes potential hemolytic effects associated with hypertonic or hypotonic compositions. The isotonic condition corresponds to a solution osmolarity from about 240 mOsmol/L to about 340 mOsmol/L (e.g., 240, 250, 260, 270, 280, 290, 300, 310, 320, 330, or 340 mOsmol/L), which is preferable in the present invention. More preferably, a substantially isotonic condition is achieved at an osmolarity of about 290 mOsmol/L.

In some instances, however, depending on the desired properties of the TFPI or TFPI variant composition (e.g., pH and osmolarity) to be maintained, the acid used as a buffering agent can be a salt form of the acid or a mixture of the acid and its salt form. In this case, a preferred buffer is a mixture of an acid and its salt form. The acid can be, for example, citric acid, succinic acid, phosphoric acid, glutamic acid, maleic acid, malic acid, acetic acid, tartaric acid, and aspartic acid. The salt form of the acid can be the sodium, potassium, calcium, or magnesium salt of its conjugate base. Especially preferred buffers are those in which the salt of the conjugate base is in the sodium form. Such buffers include citric acid/sodium citrate, succinic acid/sodium succinate, phosphoric acid/sodium phosphate, glutamic acid/sodium glutamate, maleic acid/sodium maleate, malic acid/sodium malate, acetic acid/sodium acetate, tartaric acid/sodium tartarate, and aspartic acid/sodium aspartate. When arginine is used as a solubilizing agent, even in its free base form, a preferred buffer is citric acid/sodium citrate or succinic acid/sodium succinate. In this case, the concentration of the buffer is preferably from about 5 mM to about 30 mM (e.g., 5, 10, 15, 20, 25, or 30 mM), more preferably about 20 mM.

When using the combination of an amino acid base buffered by an acid substantially free of its salt form, near isotonic formulations having higher concentrations of stabilizing amino acid are possible than can be achieved with the use of a buffer system that is a mixture of an acid and its salt form. The higher concentrations of the solubilizing agent associated with substantially isotonic compositions in such cases also result in improved TFPI or TFPI variant stability, and thus increased storage life.

For example, when citric acid is used to buffer arginine base added to an aqueous formulation comprising TFPI or TFPI variant and having a pH of 5.5, the concentration of arginine can be increased to 300 mM while still maintaining isotonicity of the formulation. This results in nearly a 35% increase in TFPI or TFPI variant storage shelf life at 50° C. Although a similar TFPI or TFPI variant storage shelf life can be achieved using the same arginine concentration and citric acid/sodium citrate as the buffering agent, arginine must be added in its acidic form to achieve a similar pH, and the resulting formulation is hypertonic. The ability to use higher concentrations of an amino acid as the primary stabilizing agent eliminates the need for more traditional TFPI or TFPI variant solubilizing agents, such as bovine serum albumin or human serum albumin, which are less desirable stabilizing agents because of potential viral contamination.

Additional Stabilizing Agents

TFPI or TFPI variant compositions of the invention may contain other compounds that increase the effectiveness or promote the desirable qualities of TFPI or TFPI variant, as long as the primary stabilizing effect achieved with an amino acid solubilizing agent combined with an antioxidant is not adversely affected. For example, TFPI or TFPI variant polypeptide degradation due to freeze thawing or mechanical shearing during processing of the TFPI or TFPI variant compositions of the present invention can be inhibited by incorporating surfactants therein in order to lower the surface tension at the solution-air interface. Suitable surfactants are nonionic surfactants, including polyoxyethylene sorbitol esters such as polysorbate 80 (Tween 80) and polysorbate 20 (Tween 20); polyoxypropylene-polyoxyethylene esters such as Pluronic F68; polyoxyethylene alcohols such as Brij 35; simethicone; polyethylene glycol such as PEG400; lysophosphatidylcholine; and polyoxyethylen-p-t-octylphenol such as Triton X-100. Classic stabilization of pharmaceuticals by surfactants or emulsifiers is described, for example, in Levine et al. (1991) *J. Parenteral Sci. Technol.* 45(3):160-165. A preferred surfactant employed in the practice of the present invention is polysorbate 80.

Other stabilizing agents, such as albumin, can optionally be added to further enhance the stability of the TFPI or TFPI variant compositions. The amount of albumin can be added at concentrations of about 1% w/v or less. Sugars or sugar alcohols may also be included in the TFPI-containing or TFPI variant-containing compositions of the present invention. Any sugar, such as a mono-, di-, or polysaccharide or a water-soluble glucan (e.g., fructose, glucose, mannose, sorbose, xylose, maltose, lactose, sucrose, dextran, pullulan, dextrin, cyclodextrin, soluble starch, hydroxyethyl starch and carboxymethylcellulose-Na), may be used. Sucrose is the most preferred sugar additive. Sugar alcohols (i.e., $C_4$-$C_8$ hydrocarbons having an —OH group), for example, mannitol, sorbitol, inositol, galactitol, dulcitol, xylitol, or arabitolm can be used. Mannitol is the most preferred sugar alcohol additive. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. Preferably, the sugar or sugar alcohol concentration is between about 1% w/v and about 15% w/v, more preferably between about 2% w/v and about 10% w/v.

Preparation of Stable Compositions

Compositions of the present invention preferably are prepared by premixing the solubilizing agent, antioxidant, optional buffer, and any other excipients prior to incorporation of TFPI or TFPI variant. Following addition of a preferred amount of solubilizing agent and antioxidant to achieve increased stability of TFPI or TFPI variant, the pH of the composition can be adjusted, preferably within a range disclosed herein that is optimal for TFPI or TFPI variant. Although pH can be adjusted following addition of TFPI or TFPI variant, preferably it is adjusted prior to addition, as this reduces the risk of, denaturation. Appropriate mechanical devices can then be used to achieve a proper mix of constituents.

Pharmaceutical Compositions

Preferably, aqueous compositions of the present invention either are in a form that may be administered to a subject or are in a form that can be used to prepare a formulation that may be administered to a subject. Aqueous compositions comprising TFPI or TFPI variants may be formulated in a unit dosage and may be in an injectable or infusible form such as solution, suspension, or emulsion. Preferably an aqueous composition of the invention is stored in the aqueous formulation to take advantage of the increased storage stability achieved in accordance with the present invention and as outlined below. The TFPI or TFPI variant pharmaceutical composition is preferably sterilized by membrane filtration and is stored in unit-dose or multi-dose containers such as sealed vials or ampoules. Such compositions also may be frozen.

Additional methods for formulating compositions generally are known in the art and may be used to further enhance storage stability of aqueous TFPI or TFPI variant pharmaceutical compositions, provided they do not adversely affect the beneficial effects of the solubilizing agents, antioxidants, and buffers disclosed herein. A thorough discussion of formulation and selection of pharmaceutically acceptable carriers, solubilizing agents, etc. can be found in *Remington's Pharmaceutical Sciences* (1990) (18$^{th}$ ed., Mack Pub. Co., Eaton, Pa.).

The following examples are offered by way of illustration and not by way of limitation. All patents, patent applications, and references cited in this disclosure are incorporated by reference in their entirety.

EXPERIMENTAL

The following protocols were used in Examples 1-6 below to determine the effect of a particular solubilizing agent and/or antioxidant on TFPI or TFPI variant degradation and stability during storage in aqueous compositions.

Reverse Phase (RP) HPLC

RP-HPLC was performed on a Waters 626 LC system equipped with a 717 autosampler (Waters Corporation, Milford, Me.) using a Vydac 214BTP54 $C_4$ column and a Vydac 214GCC54 pre-column (Separations Group, Hesparia, Calif.). The columns were initially equilibrated with a mobile phase A (10% acetonitrile, 0.1% TFA). This RP-HPLC method detects the monomeric TFPI or TFPI variant species as a main peak. Other peaks containing single and multiple oxidized methionine residues of this protein can be resolved, as well as peaks representing acetylated and carbamylated forms of TFPI or TFPI variant.

Ion Exchange HPLC (IEX-HPLC)

Ion exchange (IEX)-HPLC was performed on a Pharmacia Mono-S HR 5/5 glass column using a Waters 626 LC system with a 717 heater/cooler autosampler as described in Chen et al., supra. The column was equilibrated with 80% mobile phase A (70:30 v/v, 20 mM sodium acetate:acetonitrile at pH 5.4) and 20% mobile phase B (70:30 v/v, 20 mM sodium acetate and 1 M ammonium chloride:acetonitrile at pH 5.4). After injection, TFPI or TFPI variant was eluted by increasing mobile phase B to 85% in 21 minutes at a flow rate of 0.7 ml/minute. The TFPI or TFPI variant eluted at approximately 16.5 minutes as a single peak and was detected by UV absorbance at 280 nm with a Waters 486 absorbance detector. Data acquisition and processing were performed on a Perkin-Elmer Turbochrom system. Protein concentration was estimated by integrating the peak area and comparing it with a standard curve generated from samples of known concentrations.

pH and Osmolarity Measurements

The solution pH of the various formulations was measured by a pH meter from Orion (Model 611, Orion Research Incorporated Laboratory Products Group, Boston, Mass.). The pH meter was calibrated by the two-buffer calibration procedure suggested by the manufacturer using a pH 4 standard (Fisher Scientific, Cat. No. SB101-500) and a pH 7 standard (Fisher Scientific, Cat. No. SB107-500).

The solution osmolarity of these formulations was measured by a Vapor Pressure Osmometer from Wescor (Model 5500, Wescor Inc., Logan, Utah). The osmometer was calibrated by two standards supplied by the manufacturer: 290 mmol/kg standard (Wescor, Reorder No. OA-010) and 1,000 mmol/kg standard (Wescor, Reorder No. OA-029).

Other Materials and Methods

The formulation buffer solution was prepared by Chiron Tech Service. Ten-cc type-I tubing glass vials and Daikyo Gummi laminated, non-siliconized stoppers were obtained for use in the following studies.

The dissolved oxygen levels in TFPI or TFPI variant vials were determined by Nova BioProfile 200. The apparent first-order rate constant estimation was performed using Kaleida-Graph® (Synergy Software, Reading Pa.) software program for the TFPI oxidation.

Example 1

Prothrombin Time Assays

Suitable prothrombin time assays are described in U.S. Pat. No. 5,888,968 and in WO 96/40784. Briefly, prothrombin time can be determined using a coagulometer (e.g., Coag-A-Mate MTX II from Organon Teknika). A suitable assay buffer is 100 mM NaCl, 50 mM Tris adjusted to pH 7.5, containing 1 mg/ml bovine serum albumin. Additional reagents required are normal human plasma (e.g., "Verify 1" by Organon Teknika), thromboplastin reagent (e.g., "Simplastin Excel" by Organon Teknika), and TFPI standard solution (e.g., 20 µg of 100% pure ala-TFPI (or equivalent thereof) per ml of assay buffer).

A standard curve is obtained by analyzing the coagulation time of a series of dilutions of the TFPI standard solution, e.g., to final concentrations ranging from 1 to 5 µg/ml. For the determination of clotting time, the sample, or TFPI standard, is first diluted into the assay buffer. Then normal human plasma is added. The clotting reaction is started by the addition of thromboplastin reagent. The instrument then records the clotting time. A linear TFPI standard curve is obtained from a plot of log clotting time vs. log TFPI concentration. The standard curve is adjusted based on the purity of the TFPI standard to correspond to the equivalent TFPI concentration of a 100% pure standard. For example, if the standard is a preparation of ala-TFPI that is 97% biochemically pure (i.e., it contains 3% by weight of molecular species without biological activity of TFPI), then the concentration of each dilution of the standard is multiplied by 0.97 to give the actual concentration of TFPI. Thus, a TFPI standard that is 1.0 µg/ml based on the actual weight per ml of a preparation which is 97% pure will be equivalent to, and treated as, a concentration of 1.0×0.97, or 0.97 µg/ml. Other measures of TFPI effectiveness in treating sepsis as well as a number of other indications are also possible, including such measurements as the reduction in 28-day all cause mortality rate and improvement in some multiple organ dysfunction (MOD) scores relative to placebo.

Example 2

Effect of L-arginine Concentration on ala-TFPI Stability in Various Compositions Ala-TFPI compositions having 0.15 mg/ml ala-TFPI final concentration at a pH of 5.5 were prepared from 0.6 mg/ml stock solutions that were buffer exchanged via dialysis, analyzed for their resulting ala-TFPI concentrations using UV/Vis spectroscopy, and diluted to the 0.15 mg/ml starting target concentration using a citric acid buffer, with or without added sodium citrate. The addition of sodium citrate was used only for those samples where the L-arginine solubilizing agent was present as L-arginine HCl, while citric acid alone was used to buffer compositions containing L-arginine base.

These solutions were then aliquoted (1 ml each) to 3-cc vials for stability storage. Enough vials were set aside for the starting time point concentration measurements. The rest of the vials were placed in a 50° C. incubator for an accelerated stability study. The solubilizing agent and buffer concentrations in compositions of the four samples, having 0.15 mg/ml ala-TFPI at a pH of 5.5, are listed below:

1) 20-150 mM L-arginine HCl solubilizing agent and 10 mM citric acid/sodium citrate buffer;
2) 20-150 mM L-arginine base solubilizing agent titrated to pH 5.5 by citric acid;
3) 100-300 mM L-arginine HCl solubilizing agent and 10 mM citric acid/sodium citrate buffer; and
4) 100-300 mM L-arginine base solubilizing agent titrated to pH 5.5 by citric acid.

At 3, 7, 14, and 30 days, the contents of each vial were transferred to a 1.7 ml microcentrifuge tube and then centrifuged at 10,000 rpm for approximately 2 minutes. After centrifugation, soluble protein in the samples was separated from aggregated/precipitated protein. The amount of soluble protein was determined by the IEX-HPLC method. (Chen et al. (1999) *J. Pharm. Sci.* 88(9):881-888). The concentration data as a function of storage time were then fitted to a first-order exponential decay model ($Y=Y_0 e^{-kt}$) to calculate the half-life during storage for the remaining soluble protein using the KaleidaGraph® graphic software.

The half-life during storage ($t_{1/2}$) values for the ala-TFPI formulations are plotted as a function of L-arginine concentration in FIG. 1. These data show an increase in ala-TFPI half-life during storage with increasing L-arginine concentration. Using the L-arginine solubilizing agent alone, the compositions exhibit a significant half-life during storage increase compared to compositions with little or no added solubilizing agent.

Example 3

Degradation Kinetics of ala-TFPI Formulations

Figure 6:
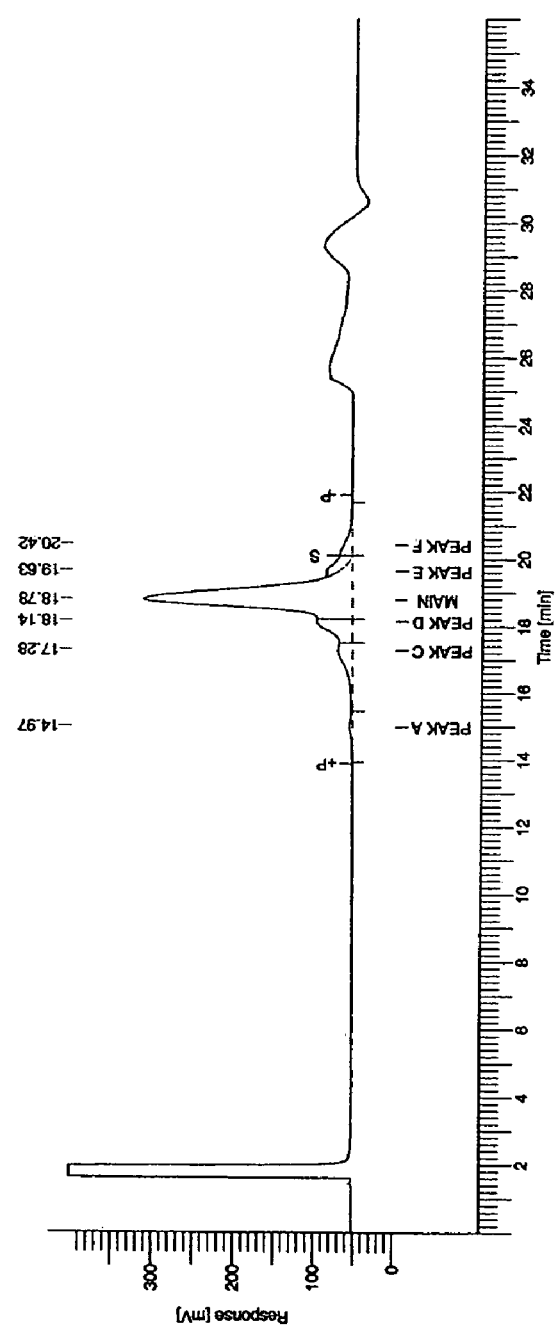
FIG. 6 is an RP-HPLC chromatogram of an ala-TFPI sample. Peaks A-F are described in Example 1.

One of the major degradation pathways for ala-TFPI during 2-8° C. storage is oxidation of methionine residues. The methionine oxidative species can be resolved as earlier eluting species to the main peak species by the reverse-phase HPLC (RP-HPLC) method. FIG. 6 is an RP-HPLC chromatogram of an ala-TFPI sample, which demonstrates the resolution of oxidized species. Peak A contains multiple MetSO species, Peak C contains single MetSO species, Peak D is norvaline-substituted ala-TFPI containing material, Peaks E and F are acetylated and/or carbamylated ala-TFPI. The Peak A and C species were integrated separately. All the rest of the species, including the main peak and peaks D, E, and F, were grouped together as the main peak species.

To understand the degradation kinetics at 30° C., 2 ml samples of ala-TFPI were prepared as described in Example 2, each containing 0.15 mg/ml TFPI, 20 mM citric acid/sodium citrate buffer, and 300 mM L-arginine. These samples were filled into 10-cc glass vials (2 ml samples in each) and incubated at 30° C. Loss of soluble protein due to aggregation/precipitation was examined first, as this phenomenon would result in a decrease in total peak area based on HPLC. After 8 weeks of storage at 30° C., the stability samples showed from 2 to 5% decrease in total peak area by both IEX-HPLC and RP-HPLC, indicating a relatively small amount of aggregation/precipitation of ala-TFPI using the above formulation. Degradation by methionine oxidation was then evaluated by plotting the main peak species, the Peak A species, and the Peak C species by RP-HPLC as a function of storage time at 30° C. Accompanying the decline in the main peak species was the rise of the Peak C species and the Peak A species. About 11% and 9% oxidized species were formed as single MetSO and multiple MetSO species, respectively, after 8 weeks of storage. This suggests that the methionine oxidation is a significant degradation pathway under standard storage conditions, based on the available detection methods. The results, shown in Table 1, also reveal that the formation of MetSO species increases with temperature.

TABLE 1

Effects of Temperature on Ala-TFPI Oxidation.

Ala-TFPI MetSO peak area (Peak C) by RP-HPLC (%)

| Temperature | Starting Material | After 4 weeks |
|---|---|---|
| 40° C. | 6.8 | 23.7 |
| 30° C. | 6.8 | 10.4 |
| 2-8° C. | 6.8 | 7.0 |

Example 4

Effect of Dissolved Oxygen on ala-TFPI Stability

Samples were prepared having the composition as described in Example 3. The level of dissolved oxygen was then varied by purging the vial headspace with a nitrogen/air displacement gas mixture via a fermentor set up. Each sample was buffered to a pH of 5.5. To facilitate equilibration of the displacement gas between the headspace and the liquid, the vials were shaken at 200 rpm for one hour while purging. Vials were then maintained at 30° C., and ala-TFPI samples were withdrawn at designated time points for stability analyses. The level of dissolved oxygen in each vial was again measured at time points for stability analysis.

Figure 2:
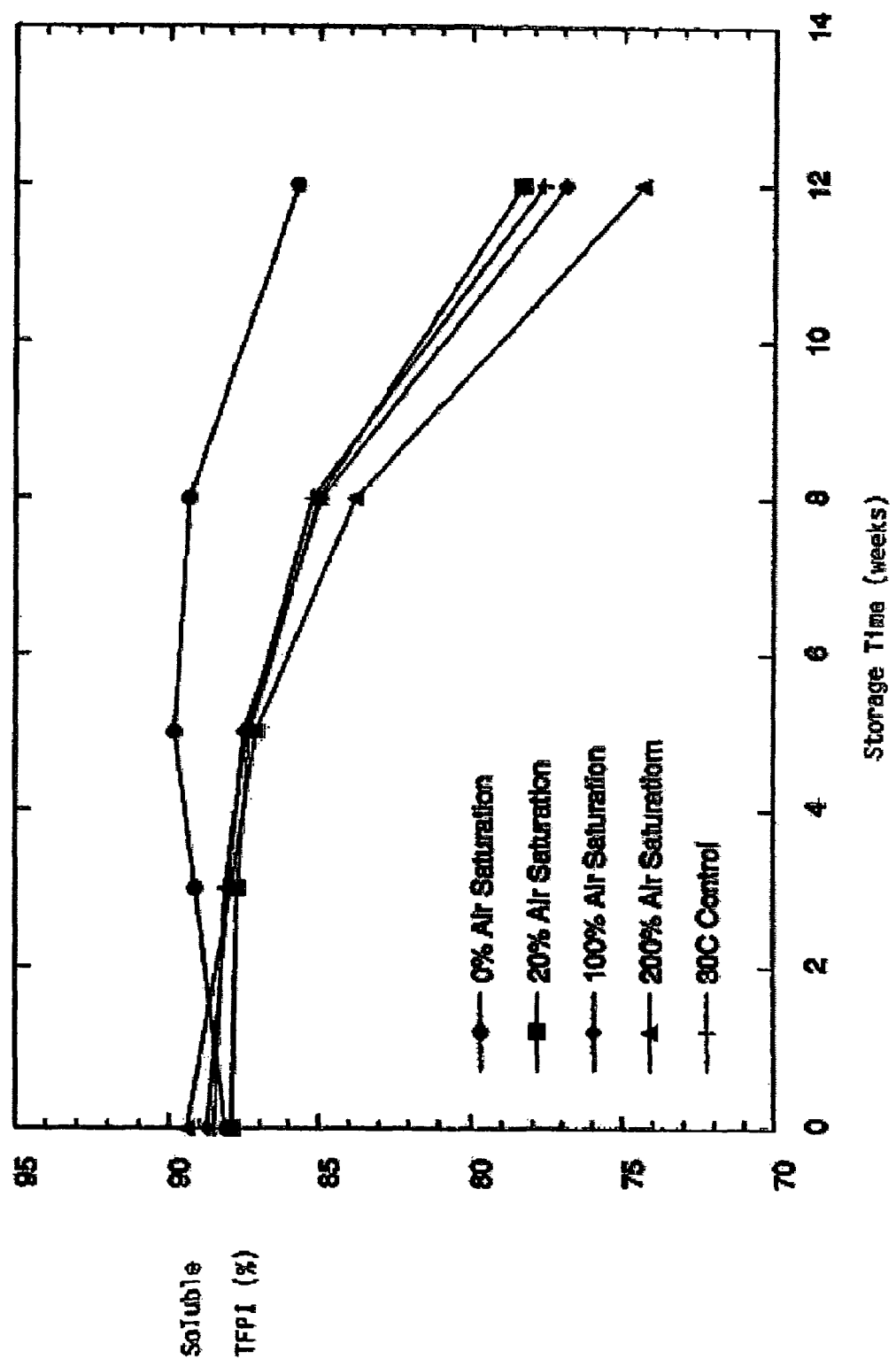
FIG. 2 shows the stability of a standard ala-TFPI composition as a function of dissolved oxygen concentration, expressed as a percentage of complete saturation with air. The percentage of soluble ala-TFPI remaining in stability samples stored at 30° C. was analyzed by reverse phase (RP) HPLC. The standard ala-TFPI composition contained 0.15 mg/ml ala-TFPI, 20 mM citric acid/sodium citrate, and 300 mM L-arginine. The pH was 5.5.

In an initial pilot study, ala-TFPI vials were prepared having dissolved oxygen levels representing 0%, 20%, 100% and 200% of air saturation (assuming 21% oxygen content at the 100% saturation condition). Results of the stability evaluation at 30° C. are shown in FIG. 2. The results indicate that ala-TFPI oxidation was substantially inhibited when the oxygen level was reduced to nearly 0% of air saturation, meaning that the atmosphere above the liquid was essentially that of pure nitrogen displacement gas. The stability improvement resulting from decreasing dissolved oxygen from 200% to 20% of air saturation, by contrast, was relatively minor.

Figure 3:
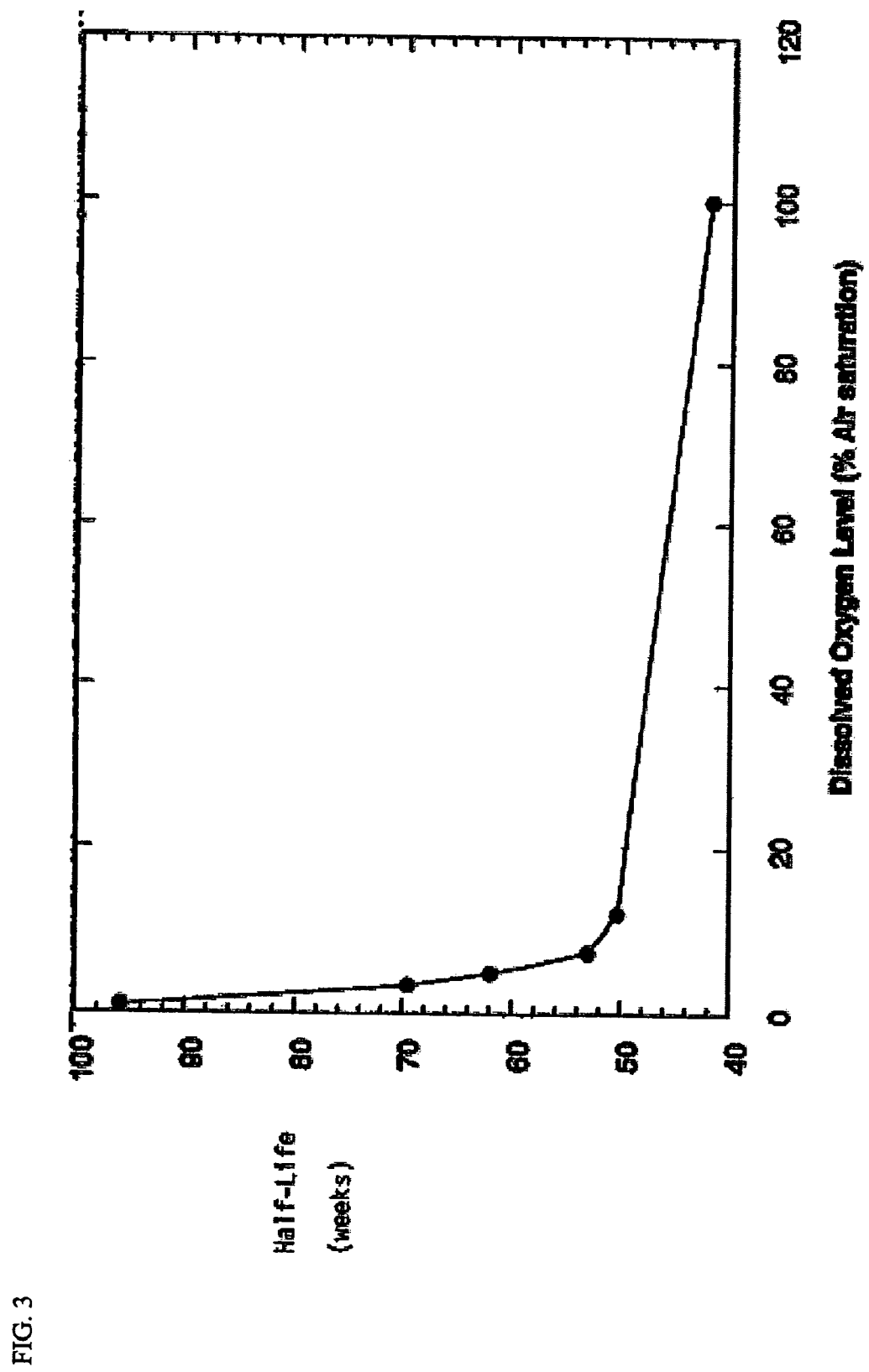
FIG. 3 shows the half-life during storage ($t_{1/2}$, in weeks) of a standard ala-TFPI composition as a function of dissolved oxygen concentration, expressed as a percentage of complete saturation with air. The percentage of soluble ala-TFPI remaining in stability samples stored at 30° C. was analyzed by RP-HPLC. The standard ala-TFPI composition contained 0.15 mg/ml TFPI, 20 mM citric acid/sodium citrate, and 300 mM L-arginine. The pH was 5.5.

A second study was then conducted to evaluate more specifically the stability performance of ala-TFPI samples having dissolved oxygen ranging from 0% to 12% of air saturation. A substantial effect on stability was found in this range. The relationship between ala-TFPI half-life during storage at 30° C. and the dissolved oxygen level is shown in FIG. 3. A dramatic improvement in ala-TFPI stability was achieved when the oxygen level in the sample was reduced to below 5% of air saturation (about 1% oxygen content). The level of dissolved oxygen in individual sample vials was also measured at the time points corresponding to the ala-TFPI concentration analyses, and no significant change in the dissolved oxygen level in the vials was observed. These results show that the use of a displacement gas such as nitrogen to displace a sufficient amount of oxygen can dramatically improve ala-TFPI storage stability if the dissolved oxygen concentration is reduced to a sufficiently low level. Displacement gases such as nitrogen are therefore deemed to be antioxidants as they inhibit the oxidation of ala-TFPI.

Example 5

Effects of Metal Chelators on ala-TFPI Oxidation

An ala-TFPI bulk solution at 10 mg/ml was diluted to 0.15 mg/ml with a buffer containing the metal chelators EDTA or DTPA at a concentration of either 1 mM or 4 mM. These compositions also contained 20 mM citric acid/sodium citrate and 300 mM L-arginine as a solubilizing agent. The diluted ala-TFPI solutions were filled into 10-cc glass vials (2 ml of sample in each) and stored at temperatures of either 2-8° C. or 30° C. for stability analysis.

Figure 4:
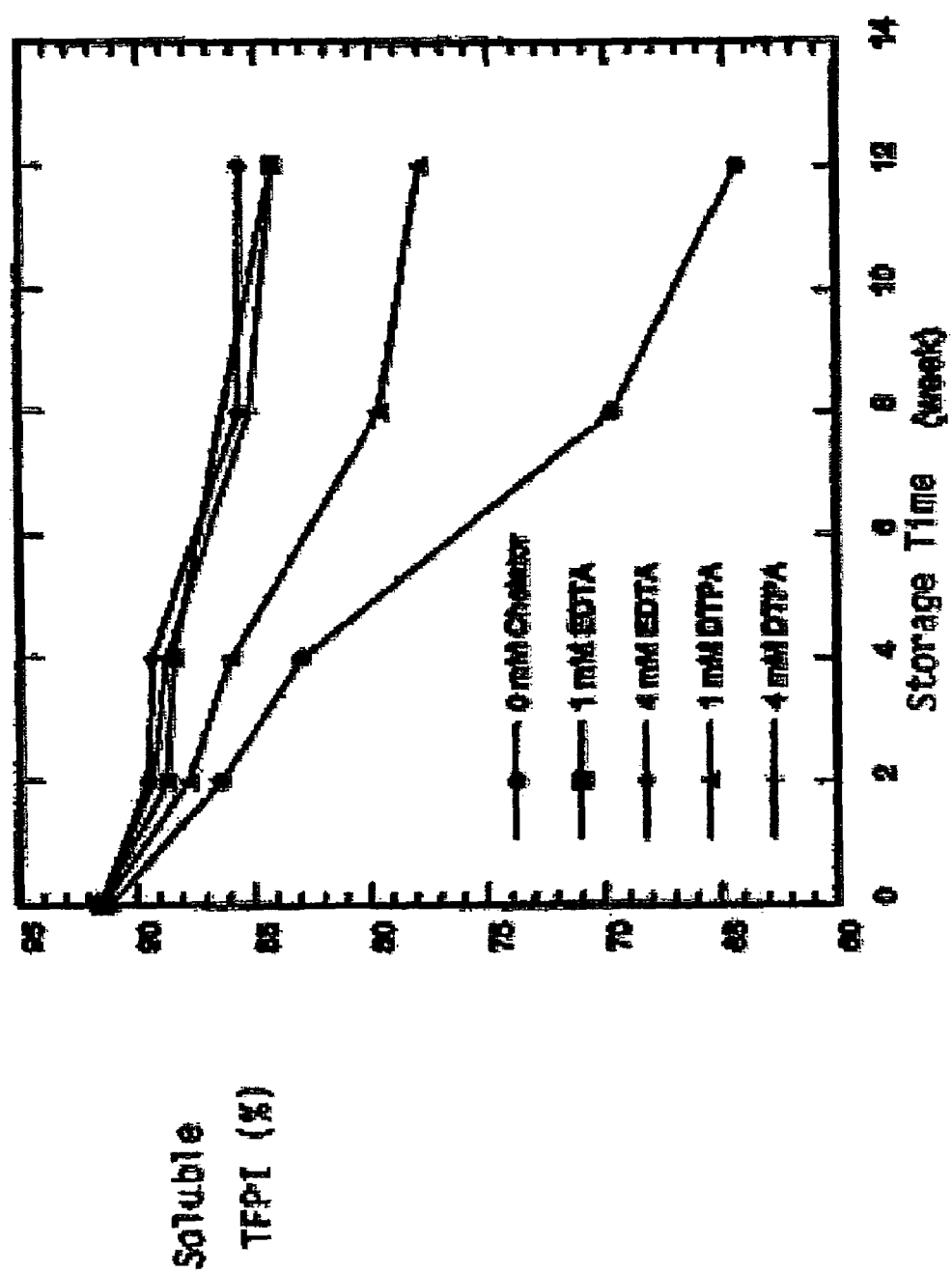
FIG. 4 shows the stability of a standard ala-TFPI composition containing the chelating agents EDTA and DTPA added in amounts of 0, 1, or 4 mM. The percentage of soluble ala-TFPI remaining in stability samples stored at 30° C. was analyzed by RP-HPLC. The standard ala-TFPI composition contained 0.15 mg/ml ala-TFPI, 20 mM citric acid/sodium citrate, and 300 mM L-arginine. The pH was 5.5.

Stability curves of the main peak area remaining at 30° C. storage temperature using RP-HPLC analysis are shown in FIG. 4. Half-life during storage data obtained from this study at both the 2-8° C. and 30° C. conditions are provided in Table 2, below. The presence of the metal chelators stabilized ala-TFPI in a concentration-dependent manner, suggesting that ala-TFPI methionine residue oxidation is catalyzed by metal ions in solution. Regardless of the actual mechanism, metal chelators serve to prevent ala-TFPI oxidation and are therefore effective as antioxidants.

Example 6

Effect of Free Methionine Amino Acid on ala-TFPI Oxidation

The 10 mg/ml ala-TFPI bulk solution was diluted to 0.15 mg/ml with a buffer containing methionine. These compositions also contained 20 mM citric acid/sodium citrate and 300 mM L-arginine as a solubilizing agent. The diluted ala-TFPI solutions were filled into 10-cc glass vials (2 ml of sample in each) and stored at temperatures of either 2-8° C. or 30° C. for stability assays.

Figure 5:
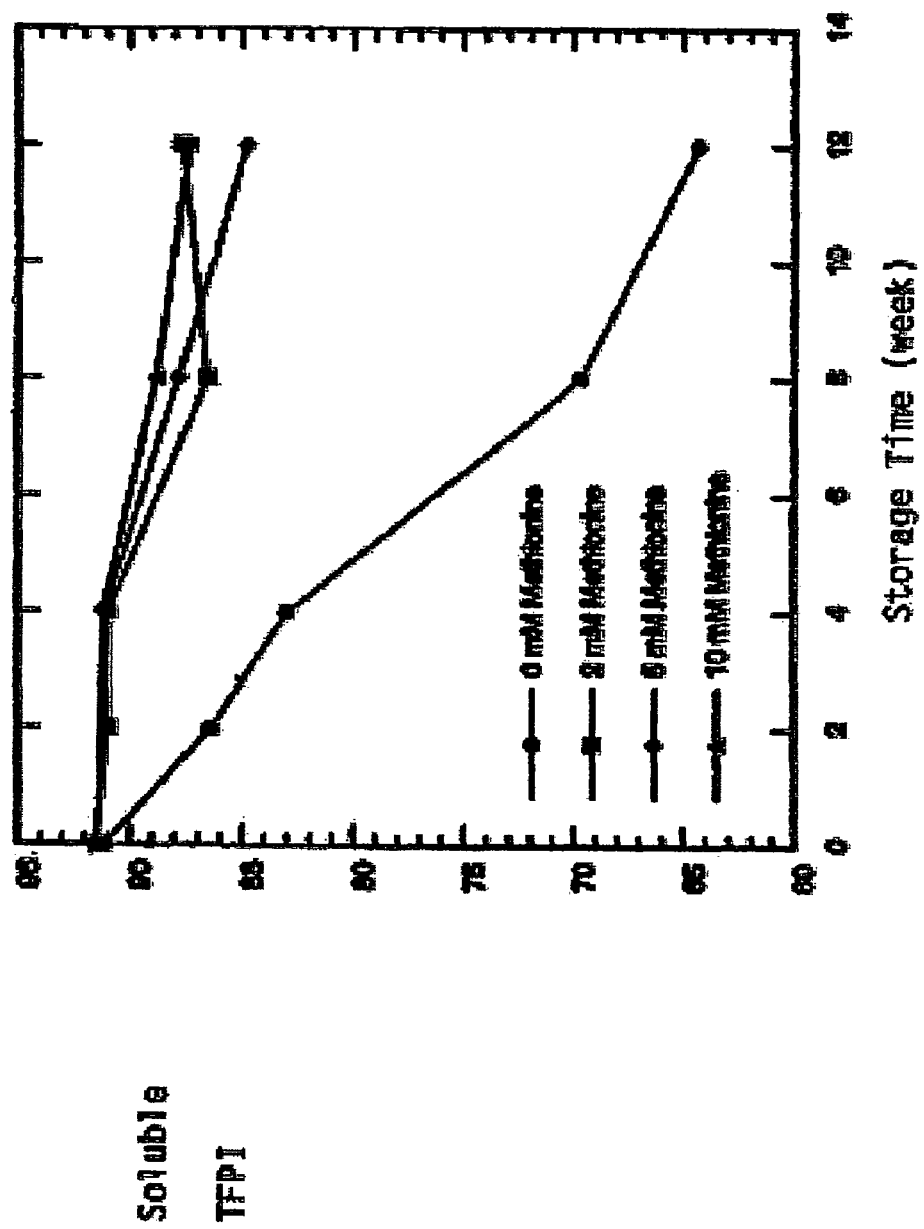
FIG. 5 shows the stability of a standard ala-TFPI composition containing the oxygen scavenger methionine added in amounts of 0, 2, 5, or 10 mM. The percentage of soluble ala-TFPI remaining in stability samples stored at 30° C. was analyzed by RP-HPLC. The standard TFPI composition contained 0.15 mg/ml ala-TFPI, 20 mM citric acid/sodium citrate, and 300 mM L-arginine. The pH was 5.5.

Stability curves of the main peak area remaining at 30° C. storage temperature using RP-HPLC analysis are shown in FIG. 5. Half-life during storage data obtained from this study at both the 2-8° C. and 30° C. conditions are provided in Table 2 below. These data show that ala-TFPI methionine residue oxidation is effectively inhibited by inclusion of 2 to 10 mM methionine in the composition. In fact, at a storage temperature of 2-8° C., no oxidative degradation of ala-TFPI was even detected in the presence of 2 to 10 mM methionine after 6 months of storage. Again, the stability of ala-TFPI compositions containing L-arginine solubilizing agent was further enhanced by the use of an antioxidant, in this case the oxygen scavenger methionine. Without being bound by any particular theory, it is believed that free methionine inhibits ala-TFPI oxidation by providing "sacrificial" methionine so that protein-bound methionine residues are less likely to be affected.

The oxidation of methionine can be caused by multiple factors, including the presence of metal ions, dissolved oxygen, and peroxide. Several antioxidants have been identified for the prevention of methionine oxidation in proteins, such as chelating agents, oxygen scavengers, reducing agents, and displacement gases. Chelating agents bind to metal ions that catalyze oxidative reactions. Oxygen scavengers react with oxygen by preferential oxidation, and thus protect the proteins by removing the source of oxidation. Reducing agents alleviate the effect of oxidants on the oxidation of proteins. Displacement gases reduce the overhead oxygen partial pressure and consequently the dissolved oxygen concentration.

The effectiveness of metal chelating agents, such as those tested in Example 4, and the oxygen scavenger methionine for reducing the ala-TFPI oxidation are compared in Table 2. Compared to the control sample (the formulation given in Example 3), containing 0.15 mg/ml ala-TFPI, 20 mM citric acid/sodium citrate buffer, and 300 mM L-arginine, all the antioxidants increased the half-life during storage of ala-TFPI. Among all the conditions evaluated, the inclusion of 10 mM methionine in the ala-TFPI formulation proved especially effective in stabilizing ala-TFPI protein against oxidation.

TABLE 2

Comparison of the Effects of Antioxidants on Ala-TFPI Stability

| Antioxidants | Half-life during storage at 2-8° C. (months) | Half-life during storage at 30° C. (months) |
|---|---|---|
| Metal Chelators (Example 4) | | |
| 1 mM EDTA | 63 | 25 |
| 4 mM EDTA | 157 | 28 |
| 1 mM DTPA | 52 | 11 |
| 4 mM DTPA | 160 | 23 |
| Oxygen scavengers (Example 5) | | |
| 2 mM methionine | No degradation detected up to six months of storage | 23 |
| 5 mM methionine | | 24 |
| 10 mM methionine | | 39 |
| Control formulation | | |
| 20 mM citrate, 300 mM arginine, pH 5.5 | 36 | 5.3 |

Example 7

Effect of ala-TFPI Protein Concentration on ala-TFPI Oxidation

The effect of ala-TFPI concentration on ala-TFPI oxidation was examined for ala-TFPI concentrations ranging from 0.15 mg/ml to 10 mg/ml. Stability samples were prepared by diluting a 10 mg/ml ala-TFPI bulk composition to 3, 1, 0.6, 0.3 and 0.15 mg/ml with the 20 mM citric acid/sodium citrate buffer used in Example 3. The samples also contained 300 mM L-arginine. Undiluted and diluted bulk samples were subsequently filled into 10-cc glass vials (2 ml of sample in each), stoppered, and stored at either 2-8° C. or 30° C. for stability evaluation.

The stability curves for the main peak remaining by RP-HPLC at both the 30° C. accelerated temperature condition and the 2-8° C. actual storage condition show that the half-life during storage of ala-TFPI depends strongly on the protein concentration with an inverse relationship. The half-lives of these stability curves are listed in Table 3. The oxidation rate increases at lower protein concentrations. Without being bound by any particular theory, we believe that it is possible that whatever the rate increase can be caused by the increased ratio of oxidants to protein molecules in solution.

TABLE 3

Half-life during storage of Main Peak Remaining by RP-HPLC for the Phase 3 TFPI at Different Concentrations after Storage at Either 30° C. or 2-8° C.

| Storage Temperature | T½ (months) during storage at protein concentration of | | | | | |
|---|---|---|---|---|---|---|
| | 10 (mg/ml) | 3 (mg/ml) | 1 (mg/ml) | 0.6 (mg/ml) | 0.3 (mg/ml) | 0.15 (mg/ml) |
| 30° C. | 22 | 28 | 9.3 | 8.5 | 6.4 | 5.6 |
| 2-8° C. | 195 | 157 | 98 | 85 | 59 | 44 |

Example 8

Survival Studies

A murine cecal ligation and puncture study was conducted to compare a freshly prepared, clinical grade lot of recombinant ala-TFPI (rTFPI) (TFPI 92) with clinical grade material that was partially deamidated and oxidized (TFPI 78). This model induces a polymicrobial intraperitoneal and systemic infection by direct fecal contamination and cecal necrosis, closely mimicking human intra-abdominal sepsis. Opal et al., *Critical Care Medicine* 29, 13-18, 2001.

Both preparations of TFPI were prepared as described in Ser. No. 60/494,546 filed Aug. 13, 2003, Ser. No. 60/509,277 filed Oct. 8, 2003, and Ser. No. 60/512,199 filed Oct. 20, 2003. These applications are incorporated by reference in their entireties. Either rTFPI 78, rTFPI 92 or diluent control was given in a blinded fashion over 48 hours (SQ q12 hours× four doses). Prior to and 48 hours after the surgical procedure, blood was drawn to determine the level of quantitative bacteremia, endotoxin and cytokines (tumor necrosis factor-alpha and interleukin-6). The animals were observed daily and deaths were recorded as they occurred. All animals underwent necropsy evaluation for histological evidence of organ injury and quantitative bacteriology at the end of the experimental period.

Figure 7:
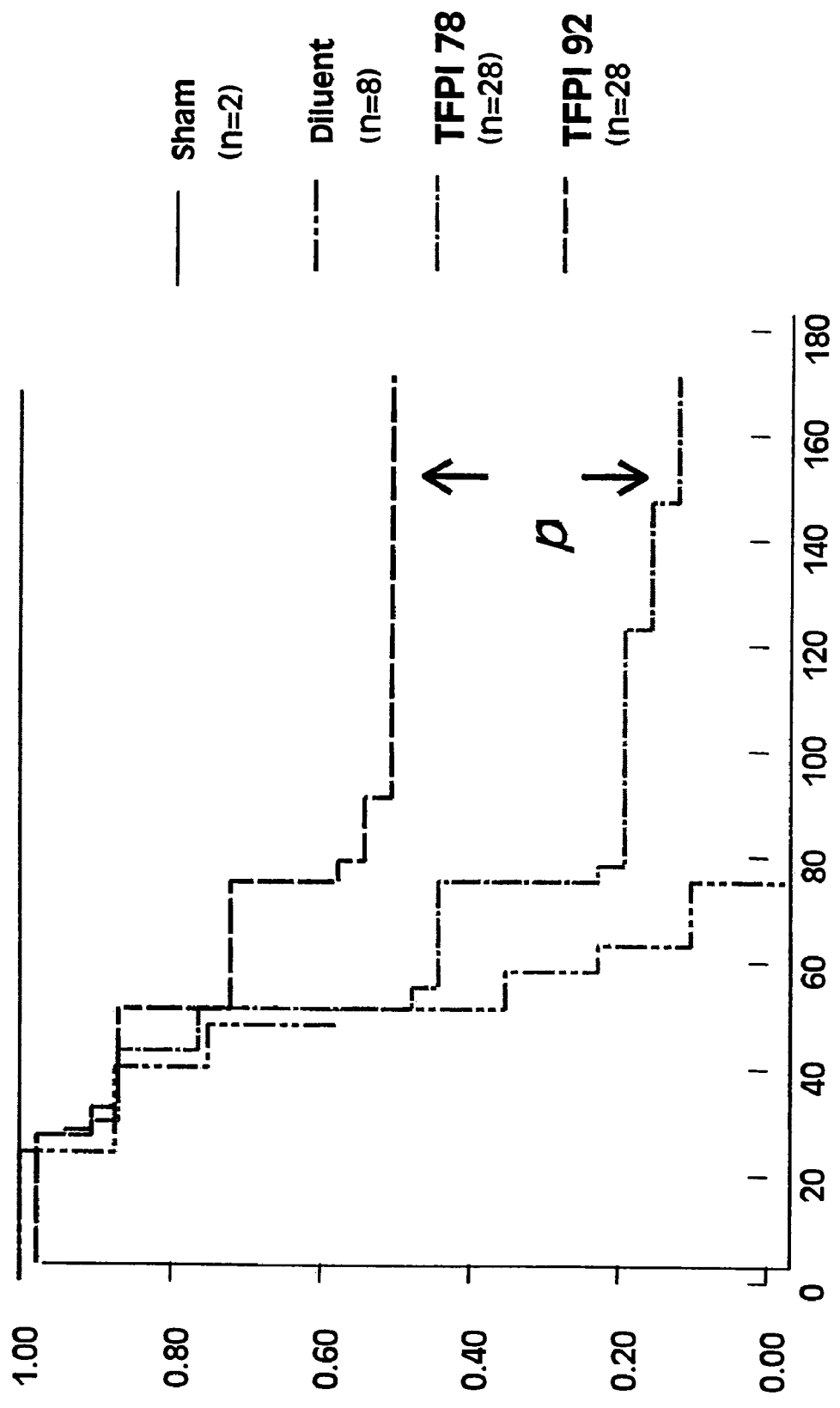
FIG. 7. Kaplan-Meier survival plots. X-axis, survival; Y-axis, time (hours).

The Kaplan-Meier survival plots are depicted in FIG. 7. There was a significant survival advantage for the mice who received the freshly prepared rTFPI as compared with the partially oxidized, deamidated form of rTFPI. Both rTFPI groups fared better than those mice that received diluent in the control group. As expected the sham-operated mice (surgical intervention with identification of the cecum but no ligation and puncture) survived the seven day study period. There were no significant differences in the secondary endpoints of bacteremia, endotoxemia, or cytokine production between the two rTFPI-treated groups.

This study demonstrates that TFPI seems to offer a survival advantage through a mechanism not explained by blood levels of bacteria, endotoxin, or cytokines. Deamidated, oxidized TFPI offered less protection than freshly prepared TFPI.

What is claimed is:

1. An aqueous composition comprising:
   (i) Tissue Factor Pathway Inhibitor (TFPI) or ala-TFPI;
   (ii) arginine in an amount sufficient to stabilize said TFPI or ala-TFPI;
   (iii) methionine in a concentration from 2 mM to 10 mM in said composition; and
   (iv) a buffer,
   wherein said buffer comprises an acid in its salt form.

2. The composition of claim 1, having a percent aggregation stability from about 45% to about 99%.

3. The composition of claim 2, having a percent aggregation stability from about 45% to about 70%.

4. The composition of claim 2, having a percent aggregation stability from about 60% to about 80%.

5. The composition of claim 2, having a percent aggregation stability from about 70% to about 90%.

6. The composition of claim 5, having a percent aggregation stability from about 80% to about 90%.

7. The composition of claim 1, having a percent oxidation stability from about 45% to about 99%.

8. The composition of claim 7, having a percent oxidation stability from about 45% to about 70%.

9. The composition of claim 7, having a percent oxidation stability from about 60% to about 80%.

10. The composition of claim 7, having a percent oxidation stability from about 70% to about 90%.

11. The composition of claim 10, having a percent oxidation stability from about 80% to about 90%.

12. The composition of claim 1, wherein said TFPI or ala-TFPI has a concentration from about 0.05 mg/ml to about 15 mg/ml in said composition.

13. The composition of claim 12, wherein said TFPI or ala-TFPI has a concentration from about 0.15 mg/ml to about 10 mg/ml in said composition.

14. The composition of claim 13, wherein said TFPI or ala-TFPI has a concentration of about 0.15 mg/ml in said composition.

15. The composition of claim 13, wherein said TFPI or ala-TFPI has a concentration of about 0.5 mg/ml in said composition.

16. The composition of claim 1, wherein said arginine has a concentration from about 50 mM to about 600 mM in said composition.

17. The composition of claim 16, wherein said arginine has a concentration from about 100 mM to about 400 mM in said composition.

18. The composition of claim 17, wherein said arginine has a concentration of about 300 mM in said composition.

19. The composition of claim 1, having a pH from about 4 to about 8.

20. The composition of claim 19, having a pH from about 5 to about 6.5.

21. The composition of claim 20, having a pH of about 5.5.

22. The composition of claim 1, wherein said buffer comprises sodium citrate.

23. The composition of claim 1, wherein said buffer has a concentration from about 5 mM to about 30 mM.

24. The composition of claim 23, wherein said buffer has a concentration of about 20 mM.

\* \* \* \* \*

SEQUENCE LISTING

<160> NUMBER OF SEQ ID NOS: 1

<210> SEQ ID NO 1

-continued

```
<211> LENGTH: 276
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
            275
```